United States Patent
Jones et al.

(10) Patent No.: US 6,894,195 B2
(45) Date of Patent: May 17, 2005

(54) PREPARATION OF 4-METHYL-2,3,5,6-TETRAFLUOROBENZYL ALCOHOL

(75) Inventors: Raymond Vincent Heavon Jones, Grangemouth (GB); Stephen Martin Brown, Huddersfield (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 10/415,262

(22) PCT Filed: Oct. 18, 2001

(86) PCT No.: PCT/GB01/04692

§ 371 (c)(1), (2), (4) Date: Apr. 25, 2003

(87) PCT Pub. No.: WO02/34707

PCT Pub. Date: May 2, 2002

(65) Prior Publication Data

US 2004/0063993 A1 Apr. 1, 2004

(30) Foreign Application Priority Data

Oct. 27, 2000 (GB) .............................................. 0026348

(51) Int. Cl.$^7$ ............................................... C07L 33/46
(52) U.S. Cl. ........................ 568/812; 560/124; 564/384; 564/385
(58) Field of Search ......................... 568/812; 560/124; 564/385, 384

(56) References Cited

U.S. PATENT DOCUMENTS 3,406,024 A * 10/1968 Richter et al. .............. 504/326
6,020,517 A * 2/2000 Monzen et al. ............. 558/425
6,362,372 B2 * 3/2002 Narizuka et al. ............ 564/385
6,452,056 B1 * 9/2002 Kawanobe et al. ......... 568/700

FOREIGN PATENT DOCUMENTS

| DE | 3714602 | 11/1988 | |
|----|---------|---------|---|
| EP | 0031199 | 7/1981 | |
| GB | 2123823 | 2/1984 | |
| GB | 2123824 | 2/1984 | |
| GB | 2127013 | 4/1984 | |
| JP | 2003089664 A | * 3/2003 | ......... C07C/17/269 |
| JP | 2003089679 A | * 3/2003 | ......... C07C/209/48 |
| WO | WO 200017138 A1 | * 3/2000 | ............ B01J/25/00 |

OTHER PUBLICATIONS

W.C. Groutas, et al., "Inactivation of leukocyte elastase by aryl azolides and sulphonate salts. Structure–activity relationship studies", Journal of Medicinal Chemistry, vol. 29, No. 7, Jul. 1986, pp. 1302–1303.

J.M. Birchall, et al., "Polyfluoroarenes part IV 2,3,4,5,6–Pentafluorotoluene and related compounds" Journal of The Chemical Society, No. 9, Sep. 1961, pp. 3719–3727.

* cited by examiner

Primary Examiner—Michael L. Shippen
(74) Attorney, Agent, or Firm—Thomas Hamilton

(57) ABSTRACT

A process for the preparation of 4-methyl-2,3,5,6-tetrafluorobenzyl alcohol comprising hydrogenating 4-methyl-2,3,5,6-tetrafluorobenzonitrile to 4-methyl-2,3,5,6-tetrafluorobenzylamine and converting 4-methyl-2,3,5,6-tetrafluorobenzylamine to 4-methyl-2,3,5,6-tetrafluorobenzyl alcohol. The process optionally also comprises the further step of reacting 4-Methyl-2,3,5,6-tetrafluobenzyl alcohol with cis-Z-3-(2-chloro-1,1,1-trifluoro-2-propenyl)-2,2-dimethylcyclopropanecarbonyl chloride to the form tefluthrin. 4-Methyl-2,3,5,6-tetrafluorobenzylamine and salts thereof are also claimed.

7 Claims, No Drawings

PREPARATION OF 4-METHYL-2,3,5,6-TETRAFLUOROBENZYL ALCOHOL

The present invention relates to a process for making polyfluorinated benzyl alcohols which are useful in the synthesis of pyrethroid pesticides, and to intermediates useful in said process.

Esters of cis-3-(haloalkenyl)-2,2-dimethylcyclopropane carboxylic acid with 4-methyl-2,3,5,6-tetrafluorobenzyl alcohol, in particular tefluthrin [2,3,5,6-tetrafluoro-4-methylbenzyl cis-3-((Z)-2-chloro-3,3,3-trifluoroprop-1-enyl)-2,2-dimethylcyclopropane carboxy]ate] are important insecticidal and acaricidal products. It is thus desirable to have an industrially acceptable and efficient process for making the necessary intermediates such as 4-methyl-2,3,5,6-tetrafluorobenzyl alcohol.

Known processes for making 4-methyl-2,3,5,6-tetrafluorobenzyl alcohol are described in DE3714602, GB2155464 and EP31199 but the processes involve reduction of the parent benzoic acids or acid halides using expensive reagents such as borohydrides, or lithiation of tetrafluorobenzene at very low temperature followed by methylation. These methods are not suited to industrial application as they involve the use of expensive reagents or require specialised low temperature conditions.

The applicants have found that these reactions may be avoided by preparing 4-methyl-2,3,5,6-tetrafluorobenzyl alcohol from 2,3,5,6-tetrafluoro-4-methylbenzonitrile and have devised a practical and efficient method of performing the process.

There is therefore provided a method for producing 4-methyl-2,3,5,6-tetrafluorobenzyl alcohol comprising:
a) hydrogenating 4-methyl-2,3,5,6-tetrafluorolbenzonitrile to 4-methyl-2,3,5,6-tetrafluoro-benzylamine; and
b) converting 4-methyl-2.3,5,6-tetrafluorobenzylamine to 4-methyl-2,3,5,6-tetrafluorobenzyl alcohol.

The hydrogenation process of step a) may be carried out according to any of the procedures in EP99622. A particularly suitable method employs hydrogen and a metal catalyst such as palladium. The reaction may be carried out at from 0° C. to about 60° C. and from ambient pressure to 10 bar of over pressure. Suitable solvents for use in the reaction include alcohols, carboxylic acids, such as formic acid, acetic acid, or mixtures of either class with water. A preferred solvent for the reaction is acetic acid or aqueous acetic acid. The mol ratio of acetic acid is suitably 2–10:1 but is preferably 4–6:1.

Step b) is preferably affected by diazotisation and in-situ hydrolytic decomposition of the diazonium salt. The reaction is suitably performed using aqueous sodium nitrite and acid at a temperature of 0–100° C., preferably 50–80° C. The acid for step b) is advantageously provided by carrying forward a solution of the benzylamine acetate salt from the hydrogenation step in a carboxylic acid such as acetic acid, after removal of the hydrogenation catalyst e.g. by filtration.

The concentration of the amine in the reaction (prior to nitrite addition) is suitably 5–30%, preferably 5–15%. The mol ratio of nitrite to amine is suitably 1–2:1 but 1:1 is preferred. After completion of the diazotisation reaction the product may contain some of an ester (e.g. acetate) ester of the desired benzyl alcohol product. The acetate ester structure is shown below.

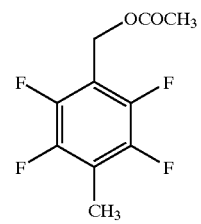

It has been found advantageous to render the reaction mass alkaline and then heat it to hydrolyse the ester to the desired alcohol compound. Once the ester has all been hydrolysed, the reaction mass is adjusted to between pH 7–10, preferably to between pH 9–10 prior to extraction of the product into a solvent for purification or for use in subsequent processes.

In a further aspect of the invention the 4-methyl-2,3,5,6-tetrafluorobenzyl alcohol is reacted with cis-Z 3-(2-chloro-1,1,1-trifluoro-2-propenyl)-2,2-dimethylcyclopropane carbonyl chloride

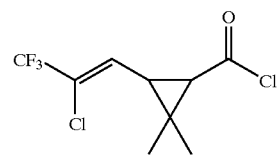

to give tefluthrin.

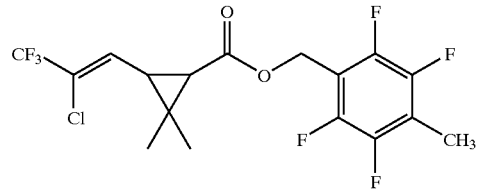

Suitable conditions for performing the reaction are described for example in EP-A-31199.

The compound 4-methyl-2,3,5,6-tetrafluorobenzylamine, and its salts are novel compounds and as such form a further aspect of the invention.

The following examples illustrate the processes and the compounds of this invention.

1H NMR was carried out on a Bruker AS 200 (200 MHz 1H) spectrometer, using TMS as reference standard. Gas chromatography analyses were obtained with a Hewlett Packard 5890 Series II. Hydrogenation reactions under pressure were carried out in a 1 litre stainless steel autoclave, fitted with a gas-inducing turbine agitator at 1000 rpm. Hydrogen feed was through a dip-pipe via a Buchi gas controller type 6002, heating and cooling was controlled by a Jelabo FP40 bath. Palladium on carbon type 58 catalyst was supplied by Johnson Matthey Ltd.

EXAMPLE 1

This Example Describes the Preparation of 4-methyl-2,3,5,6-tetrafluorobenzyl Alcohol Step a. Preparation of 4-methyl-2,3,5,6-tetrafluorobenzylamine.

A mixture of 30.0 g 4-methyl-2,3,5,6-tetrafluorobenzonitrile (0.1556 mol), 0.3 g wetting agent (Nopco 8050), 1.40 g palladium on carbon Johnson Matthey type 58 catalyst, 150 g glacial acetic acid and 217 g water was stirred under 5 barg hydrogen pressure. The reaction temperature was allowed to increase from an initial 5° C. to 30° C. over 3 hours, the reaction then being continued for a further 2 hours at which time no further hydrogen was seen to be taken up. The catalyst was removed by filtration and the solid residue washed with dichloromethane. A sample of the aqueous filtrates were evaporated to dryness and further dried under vacuum at 40° C. to give the product 4-methyl-2,3,5,6-tetrafluorobenzylammonium acetate as a white solid, melting point 113–114° C. NMR (200 MHz, $D_2O$); d 1.90 (3H, s), 2.17 (2H, m), 2.24 (3H, t, J=2.2 Hz). This solid was than used as a technical standard to estimate the strength of the remaining solution. The solution was estimated to be 3.84% 4-methyl-2,3,5,6-tetrafluorobenzylamine. This gave an overall yield. based on 583.1 g of filtrates isolated yield of 73.8%. A sample of the free amine was isolated by basification of the reaction mass. NMR (200 MHz, $D_2O$): d 2.08 (2H, m), 2.17 (3H, t, J=2.2 hz), 3.86 (2H, s)

GC-MS: M+=192.

Step b. Preparation of 4-methyl-2,3,5,6-tetrafluorobenzyl Alcohol 400 g of the 3.84% 4-methyl-2,3,5,6-tetrafluorobenzylamine solution from above (0.0795 moles) was added to a 1 litre jacketed reaction flask along with 0.2 g silicone anti-foaming agent. To this agitated solution, 28.6 g of 36 wt % aqueous sodium nitrite solution (0.149 moles) was added over 30 minutes and the temperature increased from 25° C. to 70° C. during the addition. The reaction was then held at 70° C. for a further 35 minutes. The reaction was adjusted pH 11–12 by addition of 98 g 47 wt % sodium hydroxide solution and heated to 90° C. for 1 hour. Cooling was then applied to bring the temperature to 60° C. and the pH adjusted to 8 by addition of 9 g 37% hydrochloric acid. The reaction mixture was then cooled to 25° C. and the 4-methyl-2,3,5,6-tetrafluorobenzyl alcohol product extracted into 150 ml of dichloromethane, taking care to thoroughly wash-out the reaction vessel with the solvent. The solvent was removed by evaporation to yield 17.1 g of a pink-white solid which upon analysis, against a known standard, was confirmed as 4-methyl-2,3,5,6-tetrafluorobenzyl alcohol at 90.1 wt % strength, (0.0794 moles, 99.8% yield, 73.8% overall from 4-methyl-2,3,5,6-tetrafluorobenzonitrile).

EXAMPLE 2

This Example Describes the Preparation of 4-methyl-2,3,5,6-tetrafluorobenzyl cis-3-((Z)-2-chloro-3,3,3-trifluoroprop-1-enyl)-2,2-dimethylcyclopropane carboxylate (tefluthrin)

Cis-Z 3-(2-chloro-1,1,1-trifluoro-2-propenyl)-2,2-dimethylcyclopropane carbonyl chloride (257 g) was charged to a reactor fitted with an agitator, thermometer, sub-surface nitrogen inlet and jacketed dropping funnel. Nitrogen sparging was applied to the acid chloride and maintained throughout subsequent processing. Molten 4-methyl-2,3,5,6-tetrafluorobenzyl alcohol (188.1 g) was charged to the dropping funnel. The temperature in the funnel was maintained at 80° C. The alcohol was charged to the acid chloride mixture over three hours. The maximum reaction temperature allowed during the addition was 45° C. On completion of the addition the temperature of the reaction mass was raised to 95° C. and held for 2 hours. GC analysis was used to determine if full conversion of acid chloride had occurred and that no excess reactants were remaining. The mixture was cooled to 60° C. and the molten reaction mass discharged, weighed and analysed. The reaction yielded 423.3 g of molten 4-methyl-2,3,5,6-tetrafluorobenzyl cis-3-((Z)-2-chloro-3,3,3-trifluoroprop-1-enyl)-2,2-dimethylcyclopropane carboxylate, analysis against a known standard showed this material to be 92.5 wt % giving an overall reaction yield of 96.5%.

What is claimed is:

1. A process for the preparation of 4-methyl-2,3,5,6-tetrafluorobenzyl alcohol comprising:
    a) hydrogenating 4-methyl-2,3,5,6-tetrafluorobenzonitrile to 4-methyl-2,3,5,6-tetrafluorobenzylamine using hydrogen and a palladium catalyst at from 0° C. to 60° C. and from ambient pressure to 10 bar of over pressure in a solvent selected from alcohols and carboxylic acids or mixtures either class with water; and
    b) converting 4-methyl-2,3,5,6-tetrafluorobenzylamine to 4-methyl-2,3,5,6-tetrafluorobenzyl alcohol.

2. A process according to claim 1 wherein step b) is performed by diazotisation of 4-methyl-2,3,5,6-tetrafluorobenzylamine followed by in-situ hydrolytic decomposition of the resulting diazonium salt.

3. A process according to claim 1 which process comprises the further step of reacting 4-methyl-2,3,5,6-tetrafluorobenzyl alcohol with cis-Z 3-(2-chloro-1,1,1-trifluoro-2-propenyl)-2,2-dimethylcyclopropane carbonyl chloride to form tefluthrin.

4. A process according to claim 2 in which the step of converting 4-methyl-2,3,5,6-tetrafluorobenzylamine to 4-methyl-2,3,5,6-tetrafluorobenzyl alcohol is followed by a hydrolysis reaction to convert ester by-product to the required 4-methyl-2,3,5,6-tetrafluorobenzyl alcohol.

5. A process according to claim 2 wherein the reaction mass from the hydrogenation step a) in a carboxylic acid is passed straight into the diazotisation stage (step b) after removal of the hydrogenation catalyst.

6. A process according to claim 2 wherein the reaction mass containing the 4-methyl-2,3,5,6-tetrafluorobenzyl alcohol is adjusted to pH 7–10 and the 4-methyl-2,3,5,6-tetrafluorobenzyl alcohol is extracted into a solvent.

7. 4-Methyl-2,3,5,6-tetrafluorobenzylamine, and salts thereof.

* * * * *